US00PP35810P2

(12) United States Plant Patent
Hansen

(10) Patent No.: US PP35,810 P2
(45) Date of Patent: May 14, 2024

(54) ***LIGULARIA* PLANT NAMED 'BIG GREEN TRACTOR'**

(50) Latin Name: ***Ligularia* hybrid; (*L. japonica* x *dentata*);**
Varietal Denomination: Big Green Tractor

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 90 days.

(21) Appl. No.: 17/803,936

(22) Filed: Jan. 26, 2023

(51) Int. Cl.
*A01H 5/02* (2018.01)
*A01H 6/00* (2018.01)

(52) U.S. Cl.
USPC ..... Plt./448

(58) Field of Classification Search
USPC ..... Plt./448
CPC ..... A01H 5/02; A01H 5/00; A01H 6/00
See application file for complete search history.

(56) References Cited

U.S. PATENT DOCUMENTS

PP16,113 P3 * 11/2005 Crawford ..... A01H 6/14 Plt./448
PP29,461 P3 * 7/2018 Hansen ..... A01H 5/02 Plt./448

OTHER PUBLICATIONS

ISHS Scripta Horticulturae 2016 International Code of Nomenclature for Cultivated Plants Ninth Edition, cover page and p. 30. (Year: 2016).*
Kirk-Ballard, Tractor seat plant brings color to fall, winter landscapes 2021 LSU Ag Center, retrieved on May 18, 2023 at https://www.lsuagcenter.com/articles/page1639141088238, 5 pp. (Year: 2021).*
Kiwiflora Nurseries *Ligularia* reniformis Tractor Seat, retrieved on May 18, 2023 at https://kiwiflora.co.nz/product/ligularia-reniformis-tractor-seat/, 2 pp. (Year: 2023).*

* cited by examiner

*Primary Examiner* — June Hwu

(57) ABSTRACT

The new and distinct cultivar of ornamental Goldenray plant, *Ligularia* 'Big Green Tractor', with a large mounded habit, vertical peduncle of dense clusters of large, upright, capitate, golden flowers on branched chartreuse panicles. The huge fine-textured leaves are rounded, palmately-compound, with numerous deeply-dissected lobes that have coarsely serrated and ciliolate margins. Flowering begins in late summer and lasts for about three weeks.

2 Drawing Sheets

Latin botanical classification: *Ligularia* hybrid; (*L. japonica* x *dentata*).
Variety denomination: 'Big Green Tractor'.

STATEMENT REGARDING PRIOR DISCLOSURES UNDER 37 CFR 1.77(B)(6)

The introduction of *Ligularia* 'Big Green Tractor' was in a non-enabling brief description and photograph on a website maintained by Walters Gardens, Inc. on Feb. 1, 2022. Subsequently, on Jun. 8, 2022, Walters Gardens, Inc. introduced the new plant in the "Walters Gardens 2022-2023 Catalog" with a brief non-enabling description and photograph. Walters Gardens, Inc. obtained the new plant and information about the new plant directly from the inventor. No plants of *Ligularia* 'Big Green Tractor' have been sold or offered for sale in this country or anywhere in the world, nor has any disclosure of the new plant been made more than one year prior the filing date of this application, and such sale or disclosure within one year was either derived directly or indirectly from the inventor.

BACKGROUND OF THE INVENTION

The present invention relates to a new and distinct cultivar of Golden Ray, botanically known as *Ligularia* 'Big Green Tractor', and hereinafter referred to as the cultivar 'Big Green Tractor' or the "new plant". The new plant was selected by the inventor at a wholesale perennial nursery in Zeeland, Michigan, USA as a single seedling from a cross made by the inventor from *Ligularia japonica* 'Chinese Dragon' (not patented) as the female or seed parent and 'King Kong' U.S. Plant Pat. No. 29,461 on Jul. 23, 2015. The new plant was selected from many seedlings in evaluations beginning in 2017 and the individual selected seedling was originally assigned the breeder code 15-8-3. *Ligularia* 'Big Green Tractor' has been asexually propagated through division first in spring of 2020 at the same nursery in Zeeland, MI and subsequently also by sterile plant tissue culture. Plants of 'Big Green Tractor' have been found to be stable and identical to the original selection in multiple generations of asexual propagation.

'Big Green Tractor' has not been observed under all possible environments. The phenotype may vary slightly with different environmental conditions, such as temperature, light, fertility, moisture and maturity levels, but without any change in the genotype.

BRIEF SUMMARY OF THE PLANT

*Ligularia* 'Big Green Tractor' is unique from all other *Ligularia* known to the inventor. The cultivars known to the inventor that most closely compare with the new plant include: 'Osiris Fantaisie' U.S. Plant Pat. No. 19,302, 'Britt-Marie Crawford' U.S. Plant Pat. No. 16,113, 'Hey, Mr. Wilson' (not patented), and *Ligularia* x *yoshizoeana* 'Palmatiloba'.

'Osiris Fantaisie' has a smaller habit, smaller and less incised leaves, and the foliage, peduncle, and petiole are more reddish-purple tinted. 'Britt-Marie Crawford' has a smaller habit, smaller and coarsely dentate leaves with a stronger burgundy blush. 'Hey, Mr. Wilson' has a smaller habit with smaller foliage that is more deeply dissected and more convex or folded upward along the midrib. 'Palmatiloba' has a smaller habit with smaller leaves that are less dissected and the inflorescences are lighter yellow.

The female plant has foliage that is palmately dissected to the petiole. The male parent has foliage that is more orbicular to reniform shape and coarsely dentate with a flatter margin, and the leaves, petioles, and peduncles are more reddish-purple.

The new plant, *Ligularia* 'Big Green Tractor', is distinct from all other *Ligularia* known to the inventor through the following combined characteristics:

1. Large slightly shiny foliage of dark green foliage;
2. Leaf blades are cordate to orbicular, palmately-lobed with numerous deeply incised lobes;
3. Dense rhizomes giving rise to large, broad, mounded habit;
4. Inflorescences in late summer on heavily compound branched peduncle producing a horizontally arranged group of golden yellow inflorescences.
5. Flowering period begins in late summer and is effective for about three weeks.

BRIEF DESCRIPTION OF THE DRAWINGS

The photographs of the new plant demonstrate the unique traits and the overall appearance of *Ligularia* 'Big Green Tractor'. The colors are as accurate as reasonably possible with color reproductions. Variation in ambient light spectrum, source, and direction may cause the appearance of minor variations in color. The plant used in the photographs was three years old and was grown in a nursery in Zeeland, Michigan with about 50% artificial shade and supplemental water and fertilizer when needed. No pinching or plant growth regulators have been used.

DETAILED BOTANICAL DESCRIPTION

Figure 1:
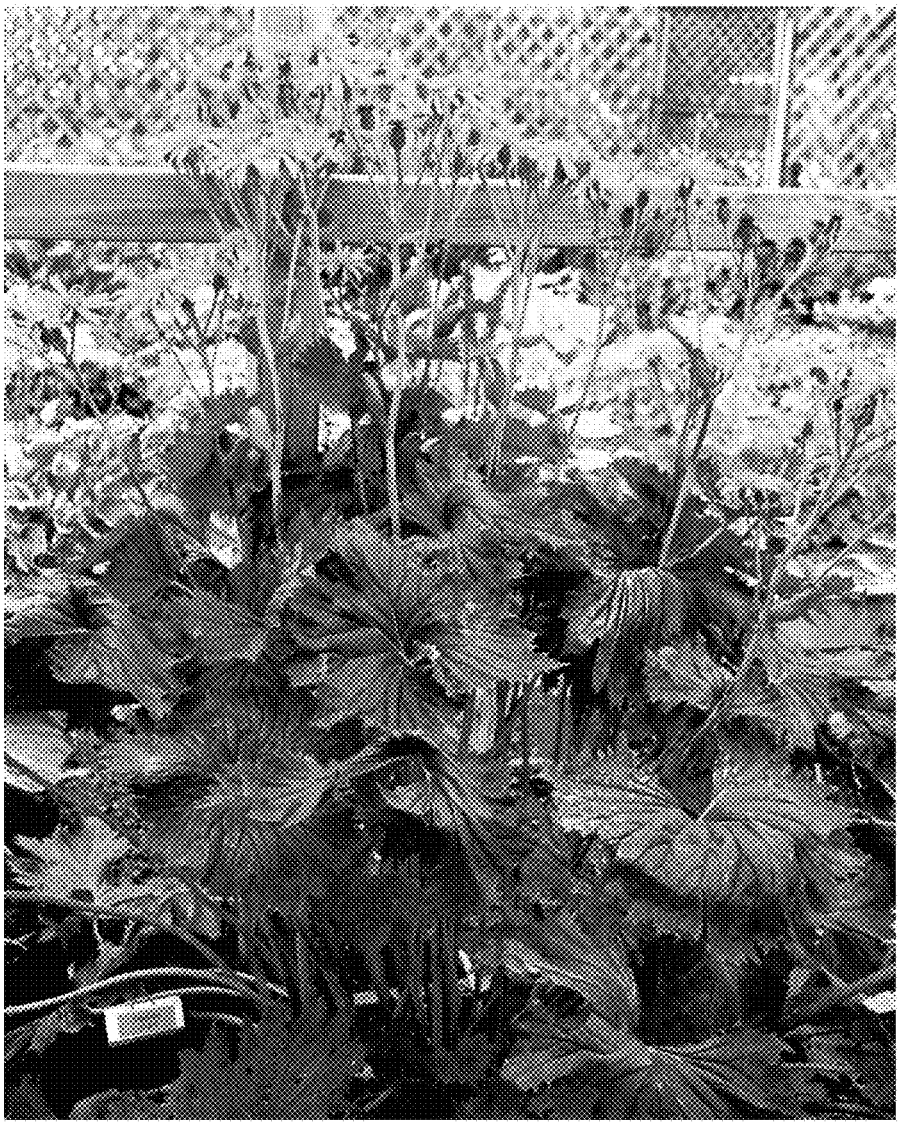
FIG. 1 shows a three-year-old plant in full flower grown in a trial garden with 50% artificial shade.
Figure 2:
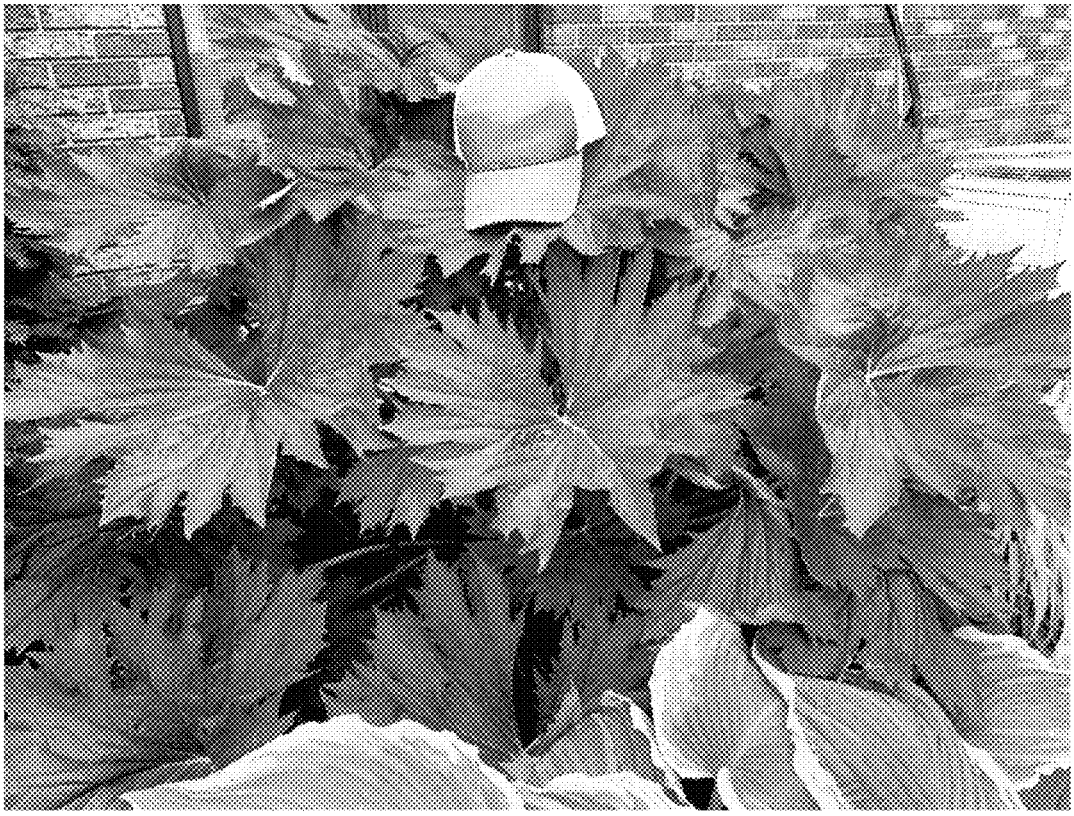
FIG. 2 shows the foliage of a five-year-old plant prior to flowering in a shaded display garden.

The following descriptions and color references are based on the 2001 edition of The Royal Horticultural Society Colour Chart except where common dictionary terms are used. *Ligularia* 'Big Green Tractor t' has not been observed under all possible environments. The phenotype may vary slightly with different growing environments such as temperature, light, fertility, soil pH, moisture, and plant maturity levels, but without any change in the genotype. The following observations and size descriptions are based on three-year-old plants growing in a 50% shaded trial garden in Zeeland, MI. Plants were given supplemental water and fertilizer but no plant growth regulators were used.

Botanical classification: *Ligularia* hybrid;

Parentage: Female or seed parent is a proprietary, unnamed, unreleased selection of *Ligularia japonica*; male or pollen parent is 'King Kong';

Plant habit: Hardy herbaceous perennial; densely rhizomatous; large, broad, mounded foliage with flowers arranged on heavily compound branched panicle above foliage; foliage height to about 92 cm tall and 150 cm wide about 90 cm above soil level, with flower height to about 138 cm tall;

Growth rate: Moderately vigorous, finishing in a 65 mm plug from a rooted Stage 3 tissue culture explants in about 10 weeks and finishing in a 3.8-liter container from a 65 mm plug in about 7 weeks;

Root: Fine, fibrous; less than 0.5 mm diameter; heavily branched; color dependent on soil type, usually white to light cream;

Stem: About ten per plant; aspect upright; puberulent; stiff; strong; about 138 cm long and about 17 mm diameter at base; primary branches to about 33 cm long and secondary branches to about 8 cm long;

Stem color: Between RHS 146D and RHS 145A;

Foliage: Glabrous; mostly acaulescent, with cauline leaves on raceme; about 20 per plant;

Leaf blade: About 4 per division; cordate to orbicular; with 15 to 19 lobes deeply incised to 7 cm; margins microciliolate and coarsely serrated with teeth about 10 to 12 mm long and 8 mm wide; rounded apex; cordate base with basal lobes imbricate; adaxial initially slightly lustrous becoming matte, abaxial matte;

Leaf blade size: Total leaf blade to about 34 cm long and about 27 cm wide; cauline leaves average about one-eighth the size of basal leaves;

Leaf blade color: At flowering adaxial nearest RHS N137B, abaxial between RHS 147B and RHS 148B; expanding adaxial nearest RHS 146C and abaxial between RHS 146D and RHS145A;

Veins: Palmate; glabrous, lustrous, and impressed on adaxial surface, pubescent proximally and puberulent distally and costate on abaxial;

Vein color: Adaxial near petiole nearest RHS 145C and distally nearest RHS137B, abaxial proximally between RHS 145A and RHS 146D and distally nearest RHS 146B;

Petiole: Terete from 3 to 8 cm from base and above, deeply fluted in basal 12 mm; fistulous; puberulent, glaucous; about 66 cm long and about 15 mm diameter at base;

Petiole color: Nearest RHS 146D distally and base between RHS 146B and RHS 147B;

Flower description:

Inflorescence: Capitate with a single row of about 15 ray florets and about 120 disc central disk florets arranged in a capitulum; inflorescence size about 65 mm across 20 mm tall; flower timing in Michigan begins late summer and continues for about three weeks on the plant;

Inflorescence about two days prior to ray florets becoming horizontal: Oblong with rounded apex and rounded base; about 2.5 cm diameter and about 2 cm tall with petals curved around apex about 10 nun above disk;

Bud color: Phyllaries nearest RHS NN137A, with exposed ray petals variable adaxial and abaxial both between RHS 23A and RHS N25A;

Capitulum: Aspect upwardly; actinomorphic; heterogamous; average size 19 mm across and 9 mm tall; average longevity on the plant, one week; self-cleaning; consisting of usually about 15 outer ray florets and about 120 central disk florets; receptacle size about 19 mm diameter and about 9 mm deep; fragrance has not been noted;

Ray floret: About 15 per capitulum; imperfect, pistillate;

*Ligule*.—One per flower; linear; margin entire; apex emarginate with indentations about 1 mm to 2 mm deep; base cuneate; glaucous and glabrous both surfaces; attitude outwardly, arcuate slightly downward in distal one-third; about 25 mm long and 4 mm wide at middle, tapering to about 1 mm at base; with typically two longitudinal ridges concave on adaxial and convex on abaxial.

*Ligule color*.—Adaxial between RHS 23B and RHS 23A, abaxial nearest RHS 12D.

*Pistil*.—Single.

*Style*.—To about 8 mm long and less than 0.5 mm diameter; beginning nearest RHS 15B and maturing to nearest RHS 21A.

*Stigma*.—Bifid in distal 1.5 mm and with maturity reflex over 360 degrees; color beginning nearest RHS 15B and maturing to nearest RHS 21A.

*Ovary color*.—Nearest RHS 144A.

Disk floret: To about 120 per head arranged in center of receptacle; perfect; tubular;

*Corolla*.—Five, about 12 mm long and 1 mm diameter; fused into tube in proximal 9 mm; acute apex; glabrous adaxial and abaxial; color nearest RHS N163C both surfaces.

*Androecium*.—Exserted; five linear anthers about 4 mm long and fused into tube around style; color nearest RHS N163C.

*Filament*.—Five, thin, about 4 mm long, and less than 0.5 mm diameter; color nearest RHS NN155B.

*Pollen*.—Abundant; color nearest RHS 17B.

*Pistil*.—Single; exserted.

*Style*.—About 15 mm long and less than 0.5 mm diameter.

*Stigma*.—Bifid in distal 1.5 mm and reflex with maturity curling around 360 degrees; style and stigma color beginning nearest RHS 15B and maturing to nearest RHS 21A.

*Ovary color*.—Nearest RHS N144A.

Pappus: Hair-like, fine, numerous about 15 per seed; about 8 mm long, less than 0.1 mm diameter, and spreading to 12 mm wide distally; color between RHS 165B and RHS 165C at maturity;

Phyllaries: Linear; acute apex and base fused; margin entire; puberulent abaxial, glabrous adaxial; to about 16 in three whorls; about 1.7 cm long and 4.5 mm wide; color nearest RHS NN137A;

Peduncle: About 10 per plant; terete, fistulous; puberulent; aspect vertical; to about 138 cm long and 15 mm diameter at base, average about 125 cm long and 13 mm diameter; with branches to about 33 cm long and about 5 mm diameter; secondary branches to about 8 cm long and 5 mm diameter; flowering portion about 15 cm tall and about 24 cm across; about 26 inflorescences per peduncle; branches to about 33 cm long and 10 mm diameter at base; aspect of primary and secondary branches upright;

Peduncle color: Between RHS I45A and RHS 146D;

Fruit: Achene; terete; about 6 mm long and 1 mm diameter; with pappus at apex; color nearest RHS 200A;

Hardiness, pest, and disease resistance: The new plant grows best with ample moisture, adequate drainage, and shade from hot sun. Hardiness at least from USDA zone 4 through high temperatures of 36° Celsius. Disease and pest resistance and susceptibility beyond what is typical of other *Ligularia* have not been observed.

The invention claimed is:

1. A new and distinct cultivar of ornamental Goldenray, *Ligularia* plant named 'Big Green Tractor', as herein described and illustrated, suitable in the landscape for foliage and flower use.

* * * * *